United States Patent [19]
Schipper

[11] Patent Number: 6,111,930
[45] Date of Patent: Aug. 29, 2000

[54] AUTOMATIC SAMPLE CHANGER FOR AN X-RAY DIFFRACTOMETER

[75] Inventor: Rolf Schipper, Karlsruhe, Germany

[73] Assignee: Bruker AXS Analytical X-Ray Systems GmbH, Karlsruhe, Germany

[21] Appl. No.: 09/192,387

[22] Filed: Nov. 16, 1998

[30] Foreign Application Priority Data

Aug. 29, 1998 [DE]  Germany .......................... 198 39 472

[51] Int. Cl.[7] .............................. G01N 23/00; B01L 3/00
[52] U.S. Cl. .............................. 378/79; 378/81; 378/208; 206/557
[58] Field of Search .................. 378/79, 80, 81, 378/208; 206/557, 558, 562; 414/222, 223, 224, 225, 226; 198/867.11

[56] References Cited

U.S. PATENT DOCUMENTS

| | | | |
|---|---|---|---|
| 3,598,992 | 8/1971 | Bridge, Jr. ................................ | 378/79 |
| 3,654,460 | 4/1972 | Payton et al. ............................ | 378/80 |
| 3,920,151 | 11/1975 | Roe ........................................ | 378/75 |
| 4,560,535 | 12/1985 | Bouchee ................................. | 206/558 |
| 4,770,593 | 9/1988 | Anderson ................................ | 378/79 |
| 5,008,082 | 4/1991 | Shaw ...................................... | 422/65 |
| 5,783,830 | 7/1998 | Hirose et al. ..................... | 250/492.21 |
| 6,028,911 | 2/2000 | Kawahara ............................... | 378/44 |

FOREIGN PATENT DOCUMENTS

| | | |
|---|---|---|
| 1 267 443 | 5/1968 | Germany . |
| 30 21 585 A1 | 12/1981 | Germany . |
| 35 12 459 A1 | 10/1986 | Germany . |

OTHER PUBLICATIONS

"Röntgendiffraktometer D 5000" by Siemens AG, 1995, Section 3.4.3, p. 3–21.
"MX Labo Genius X–ray Diffractometer", company brochure of MAC Science Co. Ltd., Yokohama, Japan.
"X–ray Diffractometer Accessories", company brochure of Scintag, Inc., Santa Clara, USA.
Photo of automatic sample changer for an X–ray diffractometer based on a robot arm offered by STOE & Cie. GmbH, Darmstadt, Germany.

Primary Examiner—David V. Bruce
Assistant Examiner—Drew A. Dunn
Attorney, Agent, or Firm—Paul Vincent

[57] ABSTRACT

A sample changer (2) for the automatic intake of a multitude of samples into the measurement position on the goniometer axis (a) of an X-ray diffractometer (20) in which the individual samples—each showing a surface, which meets the goniometer axis at a tangent in the measurement position—are linearly arranged on an insertable magazine (3). The samples on the magazine (3) can be moved in the direction of the goniometer axis (a) in order to transport each sample translationally into the measurement position. Furthermore the sample changer (2), the magazine (3) and the mountings (10) show recesses, which allow the refracted X-ray beams from the sample in transmission mode to pass through to the detector (14) unimpeded. The sample changer is suitable for reflection mode as well as transmission mode measurements without having to redesign the system.

19 Claims, 3 Drawing Sheets

AUTOMATIC SAMPLE CHANGER FOR AN X-RAY DIFFRACTOMETER

This application claims Paris Convention priority of German patent application number 198 39 472.1 filed Aug. 29, 1998, the complete disclosure of which is hereby incorporated by reference.

BACKGROUND OF THE INVENTION

The invention concerns a sample changer for the automatic intake of a multitude of samples into the measurement position on the goniometer axis of an X-ray diffractometer—with an X-ray source for the creation of X-ray radiation—and a detector for the detection of the refracted X-ray beam from a sample in the measurement position in reflection mode. In the sample changer the individual samples—each showing a surface, which meets the goniometer axis at a tangent in the measurement position—are linearly arranged on an insertable magazine.

Such a particular sample changer is known from the manual "X-Ray Diffractometer D5000", Siemens AG, 1995, section 3.4.3 "Automatic 40 Sample Changer", pp. 3–21.

X-Ray diffractometers serve as a nondestructive analysis of material samples and are standard equipment in many of today's laboratories. According to the type of sample materials to be analyzed or the analytical question, this type of diffractometric measurement of a sample surface can be carried out in reflection mode or in transmission mode via the (thin) sample. In order to be able to measure a large number of samples on a routine basis—that is one right after the other without having to manually alter the equipment—most X-ray diffractometers comprise a device which automatically picks up and changes the actually measured samples.

In the publication "MX Labo Genius X-ray Diffractometer", MAC Science Co., Ltd., Yokohama, Japan, an automatic sample changer for an X-ray diffractometer with a rotatable magazine is described, which, however, is only suitable for use in reflection mode measurements.

Likewise a company brochure titled "X-ray Diffractometer Accessories", Scintag, Inc., Santa Clara, U.S.A. describes a rotatable magazine exclusively for reflection mode measurements. This company brochure describes an azimuth scanner—used for samples to be measured in transmission mode—which only accommodates a single sample and doesn't comprise any device that automatically picks up and changes the actual sample to be measured.

An automatic sample changer for an X-ray diffractometer based on a robot arm is offered by STOE & Cie GmbH, Darmstadt, Germany. This sample changer is suited only for transmission mode measurements and, due to the robot arm construction, is a quite expensive design.

The previously quoted manual concerning the X-ray Diffractometer "D 5000" manufactured by Siemens AG describes a linear magazine for the intake and automatic conveyance of flat sample frames—in slide format—into the X-ray diffractometer's measurement position. As a result, movement of the sample frames takes place perpendicular to the measurement plane. This well-known sample changer can, on the other hand, only be used for samples intended for reflection mode measurement, since the intake mechanism would be in the way of the beam transmitted through the sample when the detector, the sample and the source are essentially linearly arranged. Moreover, reflection mode measurements with grazing incidence are only possible with this known sample changer in cases where a sample rotation—as applied during powder measurements to improve measurement statistics—can be left out.

The purpose of this invention, in contrast, is to be able to modify a sample changer of the aforementioned type with the simplest mechanical means in such a way that it can be used in reflection mode as well as transmission mode measurements without having to redesign the system, and that it easily allows sample rotation in measurement position.

SUMMARY OF THE INVENTION

According to the invention, this task is solved in a surprisingly simple and effective manner by filing the samples on the magazine in holders along the direction of the goniometer axis whereby the magazine with all samples can be moved along the direction of the goniometer axis in order to transport one sample after the other by a translational movement into the measurement position and by a sample changer, a magazine and a holder that each shows recesses, which allow in a transmission mode the X-ray beams refracted from the sample located in the measurement position to pass through to a detector unimpeded.

As a result an automatic sample change in reflection as well as in transmission measurements can be carried out without redesigning the system, whereby the reflection and the transmission measurements can be taken at random—i.e. without a fixed sequence. Up to now redesigning the diffractometer was necessary and in particular, even an automatic sequence of several transmission measurements was impossible. The new assembly concept of the inventive sample changer, however, uses a bar stock carrier, which is moved toward the goniometer axis and is perpendicular to the measurement plane. It, therefore, becomes possible during a transmission measurement to remove interfering materials underneath the sample in the measurement position from the magazine so that both measurement methods can be performed without difficulties.

In a preferred embodiment of the inventive sample changer, the respective sample—located in the measurement position—essentially remains in the magazine minimizing the space needed for the total set up.

In particular, employing a large-scale robot arm for positioning the sample is not necessary. A slight shift, e.g. by loosening a catch and rotating the sample, works just as well.

In another advantageous embodiment, mountings in the magazine make it possible to lock the samples. In this way, the samples in the magazine can be fixed, regardless of their position (even against gravity), which has considerable advantages during sample transport.

In a particularly preferred refinement of this embodiment, locking of the respective sample in the measurement position is reversible and the sample in measurement position is rotatable about an axis perpendicular to the goniometer axis. By this sample rotation in measurement position, measurement statistics can be considerably improved for powder samples, since the microcrystallite orientation in powders is averaged over all arbitrary orientations.

Another preferred embodiment of the inventive sample changer is one in which the samples are introduced into ring-shaped, preferably circular containers which can be locked in magazine mountings. Ring-shaped sample containers are per se known and the ones to be used here can also be employed with prior art equipment. The sample rings can be used with or without a bottom so that, for example, thin foils can be stretched across a ring for transmission measurements or powders whereas pastes or even liquid samples can be poured into a cup-shaped ring with a bottom.

Another particularly preferred refinement of the aforementioned sample changers comprises a groove along the ring-shaped container's circumference into which locking elements for the mountings and at least one support element and one rotatable driving roller from the sample changer can fit. As a result, a defined positioning of the sample in the measuring position is achieved. Up to now ring-shaped sample holders with circumferential grooves with this particular function have been unknown in the field of X-ray diffractometry.

In a further advantageous refinement the circumferential groove exhibits a substantially V-shaped cross-section and the support element and driving roller exhibit a round intervention cross-section in the groove—or vice versa. In this way, fine tuning of the driving and support elements allow the sample ring to be slightly raised in order to prevent friction during sample rotation in the measuring position. In order for this to take place, the driving and support elements need not even be moved in the direction in which the sample ring is to be lifted, but, in the simplest modification, can be fixed in a corresponding raised position which allows a slight lifting of the sample during intake into the measuring position.

To reduce friction during sample rotation even further, in preferred embodiments the support element can contain a rotatable bearing application in the groove's contact area, which results in a type of rolling support.

Advantageously the sample changer magazine can also include a conveyor belt—i.e. as a closed loop. In this case, the number of automatically feedable samples is not limited by the length of a rigid magazine, which extends from the goniometer support towards the laboratory space.

When changing from the reflection mode to the transmission mode, the relative angle positions of the source, sample and detector have to be variable within relatively wide limits. In reflection mode, source and detector are to be positioned on the same side of the sample surface and for transmission measurements on different sides. Usually, an X-ray diffractometer detector can be moved. In addition, the sample changer with an inserted magazine should advantageously be rotatable by at least 40°—preferably by at least 90°—about the goniometer axis and/or the X-ray source—for fixed sample changer—by at least 40°, preferably by at least 90°.

Further advantages of the invention arise from the description and the drawing. The aforementioned and the following comments can each be used individually or in arbitrary combinations. The procedures presented and described are not to be understood as a final enumeration, but they are more of an exemplary nature as an account of the invention. In the drawing:

DESCRIPTION OF THE PREFERRED EMBODIMENT

Figure 1:
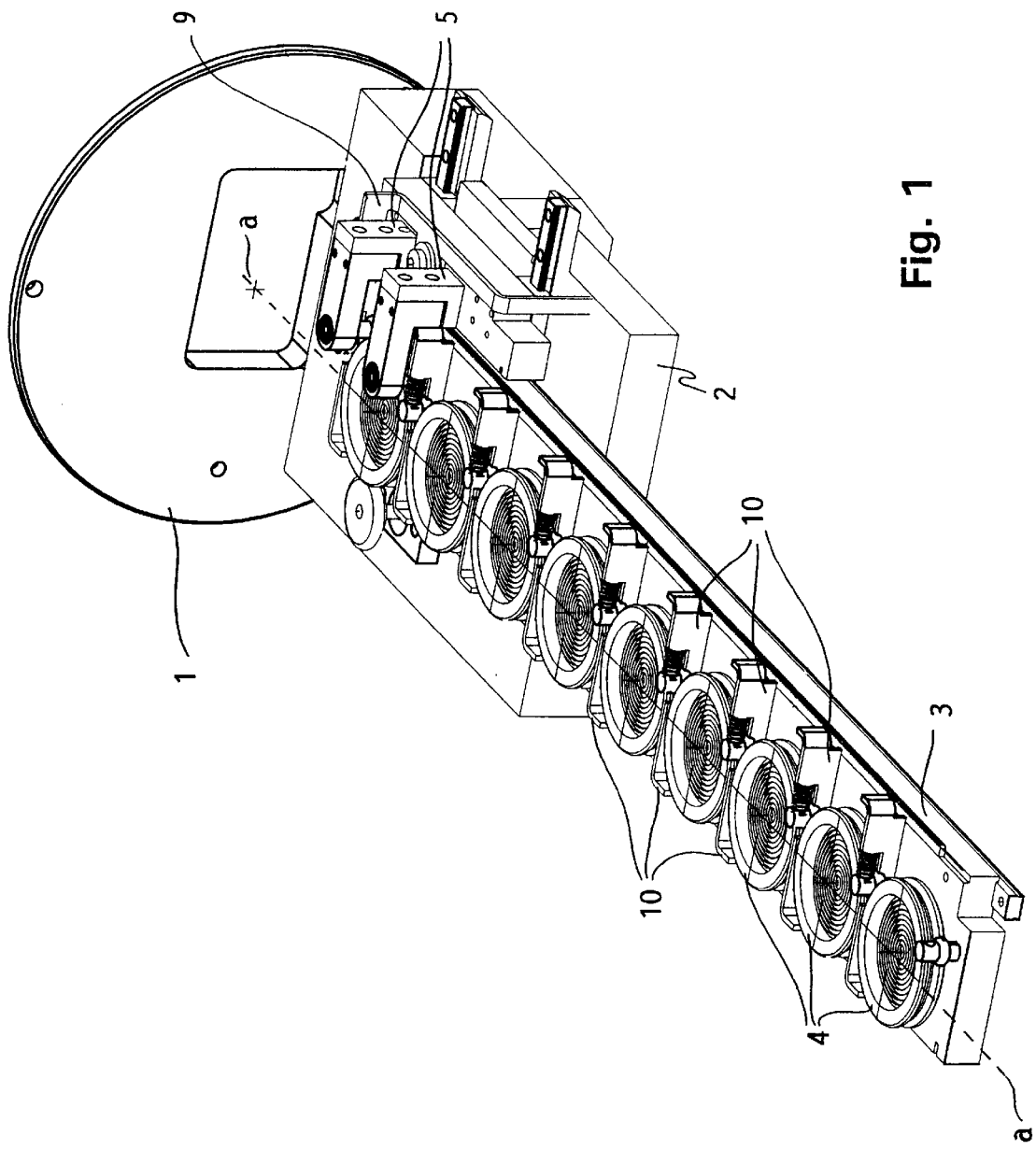
FIG. 1 shows a schematic 3-dimensional diagram of the sample changer according to the invention (angled top view)
Figure 3:
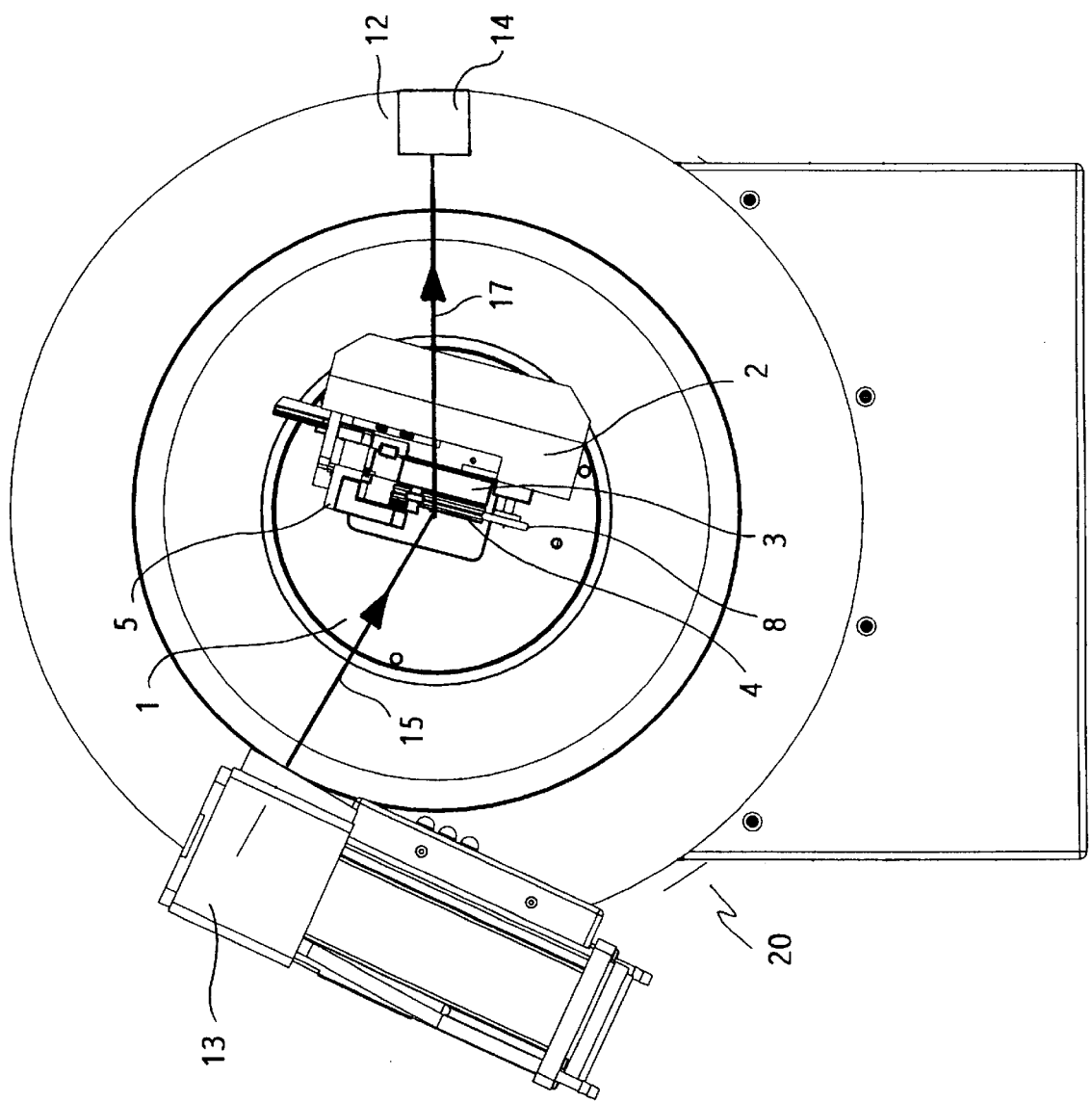
FIG. 3 shows a schematic top view of a goniometer table along the axis with an attached sample changer according to the invention in transmission mode.

In FIG. 1 a multiple sample changer (2) is fastened onto an intake plate (1), into which a linear magazine (3) is inserted—containing a multitude of ring-shaped containers (4) filed along the goniometer axis (a) in mountings (10). Measurement samples can be inserted into the containers (4). The magazine (3) can be shifted along the goniometer axis (a) by a translational movement in order to linearly transport the sample to be measured next into the measurement position of a schematically depicted (FIG. 3) X-ray diffractometer (20) with an X-ray source (13), a detector (14) and a goniometer (12), upon which the intake plate (1) is fastened.

The distances between the sample rings (4) in the magazine (3) from center to center are 55 mm, whereas the sample rings (4) themselves have a diameter of 51.5 mm and a height of 8.5 mm or 20 mm each.

Figure 2:
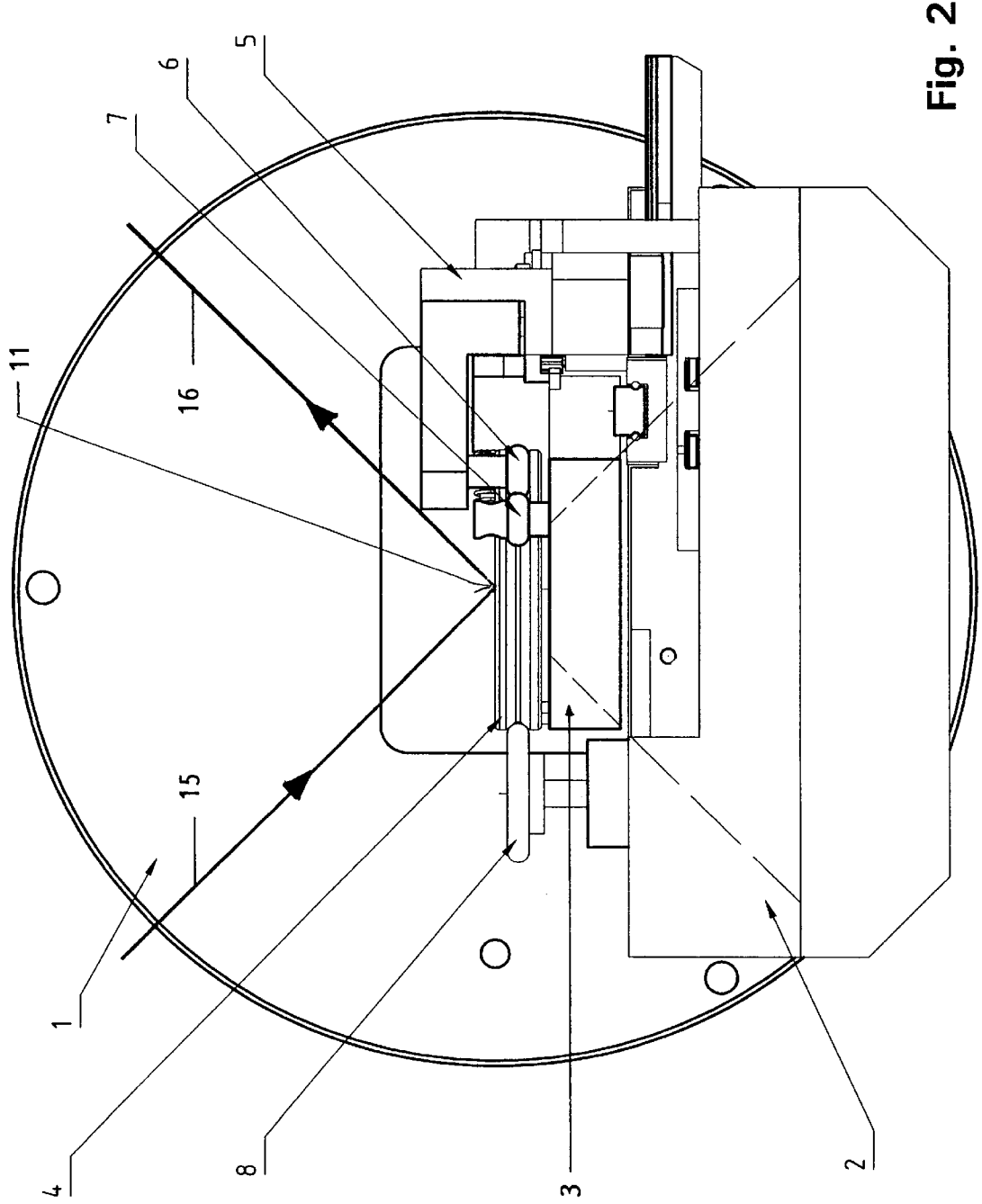
FIG. 2 shows a schematic side view of the sample changer according to the invention along the goniometer axis for measurement set-up in reflection mode.

In FIG. 2 the sample changer (2) is depicted in more detail long the goniometer axis (a) in reflection mode. The incoming X-ray beam is marked with reference number (15) and the X-ray beam reflected off a sample surface (11) with number (16). Note that for such reflection measurements the sample rings (4) of FIG. 1 have to be filled to the rim (11) with sample material.

When measuring a sample, the following steps are required:

The sample rings (4) are located in magazine (3), where they are firmly attached so as not to fall out during rotation of the entire sample changer (2) about the goniometer axis. During automatic sample change, the magazine (3) is linearly shifted by a driving motor—located in the sample changer (2)—through the goniometer center by one sample position. The direction of this movement is parallel to the goniometer axis (a).

To measure a sample, a stage (5)—upon which two bearings (6) are attached—is brought linearly up to the sample ring (4). The bearings (6) enter into the sample ring groove, which is machined with sufficient precision with respect to the surface (11) of the sample ring (4) corresponding to the measuring plane. The two bearings (6) press the sample ring (4) sideways approx. 1 mm from its original position so that the sample ring (4) is lifted from fixed support pegs (7). It is then pushed against a rotatable drive roller (8) which is also transferred into the sample ring (4) groove and rotates it during the measuring process.

A control lever (9)—moved by a cam pushes the mounting (10)—now acting as a fixing lever—away from the sample ring (4) so that the rotation of the sample ring waiting to be measured is released. This three-point bearing with two bearing rollers (6) and a driving wheel (8) allows for a precise holding and rotation of the sample ring (4) underneath the measurement plane (11) so that a measurement under 0° can be carried out with sample rotation.

After the measurement is finished, the process runs in reverse. The fixing lever (10) reaches into the sample ring (4) and squeezes it against the fixed support pegs (7). The stage (5) withdraws and makes room for further transportation of the magazine (3).

For sample measurements in transmission mode, the entire multiple sample changer (2) is rotated on the goniometer (12) about the goniometer axis (a). By doing so, the incoming X-ray beam (15) from the X-ray source (13) hits the sample at an angle larger than 40° and is not refracted on the sample surface but, instead, irradiates through the sample and sample ring (4) and, as a result, is deflected from its direction. Along the irradiation direction, sample ring (4), magazine (3) and sample changer (2) are free from material so that an open irradiation range larger than ±30° results with respect to the straight irradiation direction. The radiation beam transmitted toward the detector (14) is designated by reference number (17) in FIG. 3, which depicts an overall picture of an X-ray diffractometer (20) with a sample changer (2) according to the invention viewed along the goniometer axis (a). For this kind of transmission measurements, a foil-like sample is usually stretched across the sample ring (4) (not further depicted in the diagram).

I claim:

1. A sample changer for automatic intake of a multitude of samples into a measurement position on a goniometer axis of an X-ray diffractometer containing an X-ray source for the creation of X-ray radiation and a detector for the detection of a refracted X-ray beam from a sample in the measurement position in a reflection mode wherein in the sample changer the individual samples, each showing a surface which meets the goniometer axis at a tangent in the measurement position, are linearly arranged on an insertable magazine and wherein the samples are filed in mountings in fixed positions along the goniometer axis, wherein the magazine can be moved along the direction of the goniometer axis in order to transport each sample translationally into the measurement position and wherein the sample changer, the magazine and the mountings show recesses, which allow the X-ray radiation refracted in a transmission mode from the sample in the measurement position to pass through to the detector unimpeded.

2. The sample changer according to claim 1 wherein in the measurement position the respective samples remain in the magazine during measurement.

3. The sample changer according to claim 2 wherein the mountings in the magazine allow the samples to be locked.

4. The sample changer according to claim 3 wherein in the measurement position the locking of the respective sample can be released and the sample in the measurement position is rotatable about an axis perpendicular to the goniometer axis.

5. The sample changer according to claim 4 wherein the samples are introduced into ring-shaped, circular containers, which can be locked in the magazine mountings.

6. The sample changer according to claim 5 wherein the ring-shaped containers each comprise a groove along its circumference into which locking elements of the mountings and at least one support element and one rotatable driving roller from the sample changer fit.

7. The sample changer according to claim 6 wherein the groove exhibits a substantially V-shaped cross-section and the support element and driving roller exhibit a round intervention cross-section in the groove—or vice versa.

8. The sample changer according to claim 7 wherein the support element exhibits a rotatable bearing for contact with the groove.

9. The sample changer according to claim 1 wherein the magazine includes a conveyor belt preferably in the form of a closed loop.

10. The sample changer according to claim 8 wherein the X-ray source with fixed sample changer is rotatable by at least 40° about the goniometer axis.

11. The sample changer according to claim 8 wherein the X-ray source with fixed sample changer is rotatable by at least 90° about the goniometer axis.

12. The sample changer according to claim 1 wherein the X-ray source with fixed sample changer is rotatable by at least 40° about the goniometer axis.

13. The sample changer according to claim 1 wherein the X-ray source with fixed sample changer is rotatable by at least 90° about the goniometer axis.

14. The sample changer according to claim 8 wherein the magazine includes a conveyor belt preferably in the form of a closed loop.

15. The sample changer according to claim 8 with an inserted magazine that is rotatable by at least 40° about the goniometer axis.

16. The sample changer according to claim 8 with an inserted magazine that is rotatable by at least 90° about the goniometer axis.

17. The sample changer according to claim 8 wherein the X-ray source with fixed sample changer is rotatable by at least 40° about the goniometer axis.

18. The sample changer according to claim 8 wherein the X-ray source with fixed sample changer is rotatable by at least 90° about the goniometer axis.

19. A sample changer for automatic intake of a multitude of samples into a measurement position on a goniometer axis of an X-ray diffractometer containing an X-ray source for the creation of X-ray radiation and a detector for the detection of a refracted X-ray beam from a sample in the measurement position, the sample changer comprising:

a linear sample magazine with linearly arranged fixed positions for the multitude of samples which sample magazine is movable along the goniometer axis.

* * * * *